United States Patent
Twomey

(10) Patent No.: US 8,968,298 B2
(45) Date of Patent: Mar. 3, 2015

(54) ELECTROSURGICAL INSTRUMENT

(75) Inventor: John R. Twomey, Longmont, CO (US)

(73) Assignee: Covidien LP, Mansfield, MA (US)

( * ) Notice: Subject to any disclaimer, the term of this patent is extended or adjusted under 35 U.S.C. 154(b) by 456 days.

(21) Appl. No.: 13/421,373

(22) Filed: Mar. 15, 2012

(65) Prior Publication Data

US 2013/0245623 A1    Sep. 19, 2013

(51) Int. Cl.
*A61B 18/14* (2006.01)

(52) U.S. Cl.
CPC ..... *A61B 18/1445* (2013.01); *A61B 2018/1455* (2013.01)
USPC .................. 606/38; 606/37; 606/41; 606/51; 606/180

(58) Field of Classification Search
CPC ............... A61B 2018/1452; A61B 2018/1455; A61B 2018/146; A61B 18/14; A61B 18/1442; A61B 18/1445
USPC ........... 606/32, 37–41, 45–52, 167, 170, 171, 606/180
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |

(Continued)

FOREIGN PATENT DOCUMENTS

| | | |
|---|---|---|
| CN | 201299462 | 9/2009 |
| DE | 2415263 | 10/1975 |

(Continued)

OTHER PUBLICATIONS

U.S. Appl. No. 08/926,869, filed Sep. 10, 1997, James G. Chandler.

(Continued)

*Primary Examiner* — Carl H Layno
*Assistant Examiner* — Eugene Wu

(57) ABSTRACT

An electrosurgical instrument is provided. The electrosurgical instrument includes a housing. An outer shaft extends from the housing. The outer shaft includes a bifurcated distal end having a pair of first spaced-apart members with an elongated slot extending therebetween. The pair of first spaced-apart members configured to receive tissue therebetween. An inner shaft is disposed within the outer shaft and includes a bifurcated distal end having a pair of second spaced-apart members with an elongated slot extending therebetween. The pair of second spaced-apart members is configured to receive tissue therebetween. Each of the pairs of the first and second spaced apart members includes one or more electrodes thereon. The inner shaft is rotatable from an initial configuration for positioning tissue between the pairs of first and second spaced-apart members to a subsequent configuration for compressing the tissue disposed between the pairs of first and second spaced-apart members.

20 Claims, 4 Drawing Sheets

(56) References Cited

U.S. PATENT DOCUMENTS

| | | | |
|---|---|---|---|
| 5,411,514 A | 5/1995 | Fucci et al. | |
| 5,472,439 A | 12/1995 | Hurd | |
| D384,413 S | 9/1997 | Zlock et al. | |
| H1745 H | 8/1998 | Paraschac | |
| D402,028 S | 12/1998 | Grimm et al. | |
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |
| 6,083,223 A * | 7/2000 | Baker | 606/52 |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| 6,419,684 B1 * | 7/2002 | Heisler et al. | 606/170 |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| 7,101,371 B2 * | 9/2006 | Dycus et al. | 606/49 |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 8,012,153 B2 * | 9/2011 | Woloszko et al. | 606/48 |
| D649,249 S | 11/2011 | Guerra | |
| D649,643 S | 11/2011 | Allen, IV et al. | |
| 2006/0178670 A1 * | 8/2006 | Woloszko et al. | 606/48 |
| 2008/0243126 A1 | 10/2008 | Gutierrez et al. | |
| 2010/0324446 A1 * | 12/2010 | Pendleton | 600/565 |
| 2011/0004215 A1 | 1/2011 | Bradley et al. | |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 19946527 | 12/2001 |
| DE | 10045375 | 10/2002 |
| DE | 10 2004 026179 | 12/2005 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-10223 | 1/1997 |
| JP | 9-122138 | 5/1997 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2003-245285 | 9/2003 |
| JP | 2004-517668 | 6/2004 |
| JP | 2004-528869 | 9/2004 |
| JP | 2011-125195 | 6/2011 |
| SU | 401367 | 11/1974 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 2005/110264 | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/028,810, filed Feb. 16, 2011, Robert M. Sharp.
U.S. Appl. No. 13/030,231, filed Feb. 18, 2011, Jeffrey M. Roy.
U.S. Appl. No. 13/050,182, filed Mar. 17, 2011, Glenn A. Horner.
U.S. Appl. No. 13/072,945, filed Mar. 28, 2011, Patrick L. Dumbauld.

(56) References Cited

OTHER PUBLICATIONS

U.S. Appl. No. 13/080,383, filed Apr. 5, 2011, David M. Garrison.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011, Allan J. Evans.
U.S. Appl. No. 13/212,329, filed Aug. 18, 2011, Allan J. Evans.
U.S. Appl. No. 13/212,343, filed Aug. 18, 2011, Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Homer.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/344,729, filed Jan. 6, 2012, James D. Allen, IV.
U.S. Appl. No. 13/355,829, filed Jan. 23, 2012, John R. Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/358,657, filed Jan. 26, 2012, Kim V. Brandt.
U.S. Appl. No. 13/360,925, filed Jan. 30, 2012, James H. Orszulak.
U.S. Appl. No. 13/369,152, filed Feb. 8, 2012, William H. Nau, Jr.
U.S. Appl. No. 13/400,290, filed Feb. 20, 2012, Eric R. Larson.
U.S. Appl. No. 13/401,964, filed Feb. 22, 2012, John R. Twomey.
U.S. Appl. No. 13/404,435, filed Feb. 24, 2012, Kim V. Brandt.
U.S. Appl. No. 13/404,476, filed Feb. 24, 2012, Kim V. Brandt.

Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.

(56) References Cited

OTHER PUBLICATIONS

Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.

(56) References Cited

OTHER PUBLICATIONS

Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 1.73008.1 dated Nov. 4, 2011.
Int'l Search Report EP 11 179514 dated Nov. 4, 2011.
Int'l Search Report EP 11 180182.5 dated Nov. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

ELECTROSURGICAL INSTRUMENT

BACKGROUND

1. Technical Field

The present disclosure relates to an electrosurgical instrument and, more particularly, to an electrosurgical instrument including inner and outer shafts configured to grasp and, subsequently, electrosurgically treat tissue.

2. Description of Related Art

Electrosurgical forceps are well known in the medical arts. For example, an electrosurgical endoscopic forceps is utilized in surgical procedures, e.g., laparoscopic surgical procedures, where access to tissue is accomplished through a cannula or other suitable device positioned in an opening on a patient. The endoscopic forceps, typically, includes a housing, a handle assembly including a movable handle, a drive assembly, a shaft and an end effector assembly attached to a distal end of the shaft. The end effector includes jaw members that operably communicate with the drive assembly to manipulate tissue, e.g., grasp and electrosurgically treat tissue. Typically, the endoscopic forceps utilizes both mechanical clamping action and electrical energy to effect hemostasis by heating the tissue and blood vessels to coagulate, cauterize, seal, cut, desiccate, and/or fulgurate tissue.

To operably couple the end effector to the drive assembly so that the movable handle may effect movement of the jaw members involves coupling many different and intricate components together. These components are, typically, very expensive and need to be properly positioned and/or aligned with one another during the manufacturing process of the endoscopic forceps. As can be appreciated, this may increase manufacturing time and, thus, the overall manufacturing cost of the endoscopic forceps.

SUMMARY

In view of the foregoing, it may prove useful in the medical arts to provide an electrosurgical instrument including inner and outer shafts that are configured to grasp and, subsequently, electrosurgically treat tissue Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

An aspect of the present disclosure provides an electrosurgical instrument. The electrosurgical instrument includes a housing. An outer shaft extends from the housing. In certain instances, the outer shaft may be flexible. The outer shaft includes a bifurcated distal end having a pair of first spaced-apart members with an elongated slot extending therebetween. The pair of first spaced-apart members configured to receive tissue therebetween. The pair of first spaced-apart members includes one or more corresponding first electrodes thereon adapted to connect to an electrosurgical energy source. An inner shaft is disposed within the outer shaft and includes a bifurcated distal end having a pair of second spaced-apart members with an elongated slot extending therebetween. The pair of second spaced-apart members is configured to receive tissue therebetween. The pair of second spaced-apart members include one or more corresponding second electrodes thereon adapted to connect to the electrosurgical energy source. The inner shaft is rotatable from an initial configuration for positioning tissue between the pairs of first and second spaced-apart members to a subsequent configuration for compressing the tissue disposed between the pairs of first and second spaced-apart members to facilitate electrosurgically treating the tissue.

An insulative member may be operably disposed between the pairs of first and second spaced-apart members to prevent short circuiting therebetween. The insulative member may be made from plastic, rubber or ceramic.

In certain instances, a cutting blade shaft may be translatable through the inner shaft. The cutting blade shaft may include a knife blade at distal end thereof. The knife blade is translatable with the cutting blade shaft from an initial position proximal the pair of second spaced-apart members to a subsequent position therebetween for severing tissue.

A longitudinal groove may extend along a length of each spaced-apart member of the pair of second spaced apart members and may be configured for reciprocation of the knife blade therein.

In certain instances, each of the first and second electrodes may be further defined by a plurality of intermittently-spaced electrodes.

The electrosurgical instrument may include a movable handle that is configured to rotate the inner shaft within the outer shaft to effect movement of the pair of second spaced-apart members with respect to the pair of first spaced apart members.

An aspect of the present disclosure provides an electrosurgical instrument that is configured to seal tissue. The electrosurgical instrument includes a housing having a controller operably disposed therein. The controller is configured to regulate electrosurgical energy transmitted via an electrosurgical energy source to the electrosurgical instrument. An outer shaft extending from the housing defines a longitudinal axis therethrough. The outer shaft includes a bifurcated distal end having a pair of first spaced-apart members with an elongated slot extending therebetween. The pair of first spaced-apart members is configured to receive tissue therebetween. The pair of first spaced-apart members includes one or more corresponding first electrodes thereon that are adapted to connect to the electrosurgical energy source. An inner shaft is disposed within the outer shaft. The inner shaft includes a bifurcated distal end having a pair of second spaced-apart members with an elongated slot extending therebetween. The pair of second spaced-apart members is configured to receive tissue therebetween. The pair of second spaced-apart members includes one or more corresponding second electrodes thereon that are adapted to connect to the electrosurgical energy source. The inner shaft is rotatable from an initial configuration for positioning tissue between the pairs of first and second spaced-apart members to a subsequent configuration for compressing the tissue disposed between the pairs of first and second spaced-apart members to facilitate sealing the tissue upon activation of the first and second electrodes. A ratchet mechanism is operably disposed in the housing and configured to regulate pressure applied to tissue positioned between the pairs of first and second spaced-apart members when the inner shaft is in the subsequent configuration. One or more sensors operably associated with at least one of the inner and outer shafts and configured to control a gap between the pairs of first and second spaced-apart members when the inner shaft is in the subsequent configuration.

In certain instances, the gap between the pairs of first and second spaced-apart members when the inner shaft is in the subsequent position ranges from about 0.001 inches to about 0.006 inches.

In certain instances, the pressure applied to tissue when the inner shaft is in the subsequent position ranges from about 3 kg/cm³ to about 161 g/cm³.

A longitudinal groove may extend along a length of each spaced-apart member of the pair of second spaced apart members and may be configured for reciprocation of the knife blade therein.

The present disclosure also provides a method for electrosurgically treating tissue. Tissue is positioned between pairs of first and second spaced-apart members of respective bifurcated distal ends of inner and outer shaft members of an electrosurgical instrument. The pairs of first and second spaced-apart members each may include one or more respective first and second electrodes thereon. Each of the first and second electrodes may be adapted to connect to an electrosurgical energy source that is configured to supply electrosurgical energy thereto. The inner shaft is rotated from an initial configuration to a subsequent configuration to compress tissue. Thereafter, electrosurgical energy is transmitted to the pair of second spaced-apart members to electrosurgically treat the tissue. The inner shaft is then rotated to its initial configuration.

In certain instances, the electrosurgical instrument may include a cutting blade shaft that is translatable through the inner shaft may be moved to sever the electrosurgically treated tissue.

In certain instances, electrosurgically treating tissue may include sealing tissue. For example, the method may include the step of providing the electrosurgical instrument with a sensor configured to control a gap between the pairs of first and second spaced-apart members when the inner shaft is in the subsequent configuration. Moreover, the method may include the step of providing the electrosurgical instrument with a ratchet mechanism configured to regulate pressure applied to tissue positioned between the pairs of first and second spaced-apart members when the inner shaft is in the subsequent configuration. The gap between the pairs of first and second spaced-apart members when the inner shaft is in the subsequent position may range from about 0.001 inches to about 0.006 inches and the pressure applied to tissue when the inner shaft is in the subsequent position may range from about 3 kg/cm³ to about 16 kg/cm³.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1A:
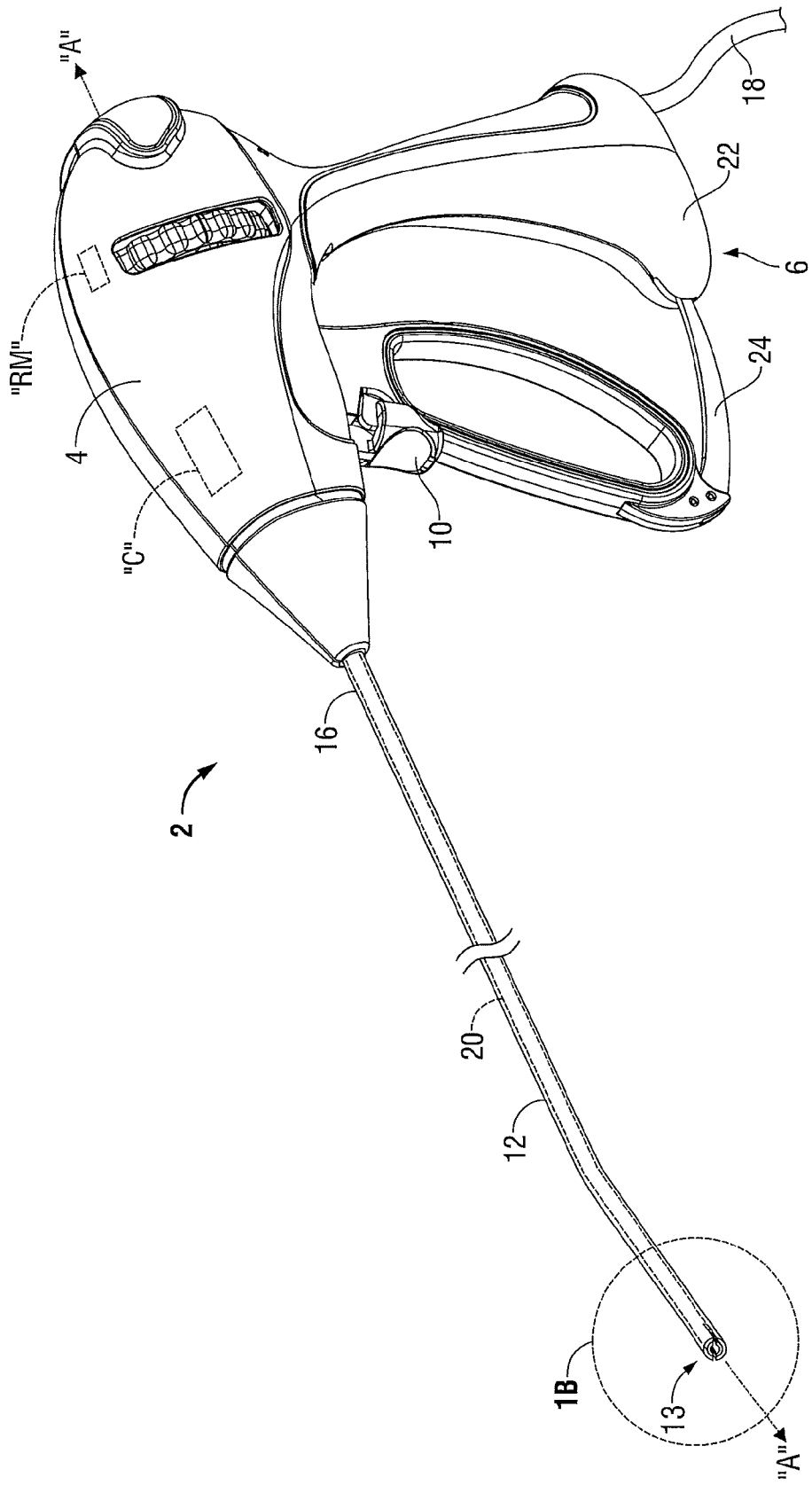
FIG. 1A is a perspective view of an endoscopic electrosurgical forceps according to an embodiment of the present disclosure.

Turning now to FIG. 1A, an electrosurgical instrument 2 (instrument 2) is provided having a longitudinal axis "A-A" defined therethrough, a housing 4, a handle assembly 6, and a trigger assembly 10. Instrument 2 further includes an outer shaft 12 having a bifurcated distal end 13 configured to engage tissue and a proximal end 16 that mechanically engages housing 4. Instrument 2 also includes electrosurgical cable 18 that connects instrument 2 to a generator (not shown) or other suitable power source. Alternatively, instrument 2 may be configured as a battery powered instrument. Cable 18 includes a wire (or wires) (not shown) that provides electrical energy to electrodes 36a, 36b, and 37a, 37b that are disposed on respective first and second spaced-apart members 21a, 21b and 15a, 15b (FIG. 1B) to electrosurgically treat tissue, as is described in greater detail below. Electrodes 26a and 37a are not shown in detail.

Housing 4 houses the internal working components of instrument 2, such as a drive assembly (not shown), working components of the handle assembly 6, electrical raceways associated with the cable 18, and other working components therein.

Figure 3A:
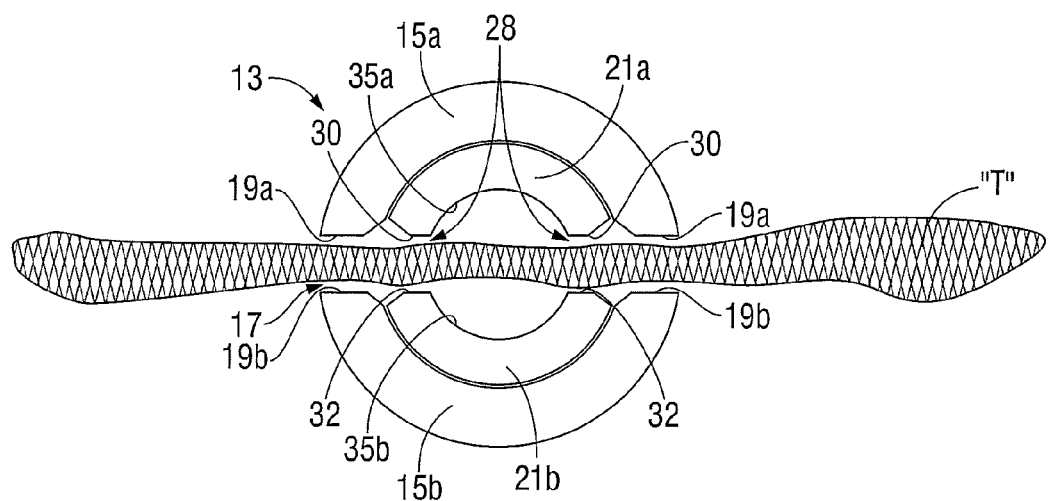
FIGS. 3A-3B are schematic, plan views of a distal end of a shaft depicted in FIGS. 1A and 1B illustrating tissue positioned thereabout and with a distal end of the shaft in open and clamping configurations, respectively.

With continued reference to FIG. 1A, handle assembly 6 includes a fixed handle 22 and a moveable handle 24. Fixed handle 22 is integrally associated with housing 4 and movable handle 24 is moveable relative to fixed handle 22. Moveable handle 24 is ultimately connected to the drive assembly such that, together, movable handle 24 and the drive assembly mechanically cooperate to impart rotational movement of an inner shaft 20 (shown in phantom in FIG. 1A) including second spaced-apart members 21a and 21b (see FIGS. 3A and 3B). In particular, moveable handle 24 is initially spaced-apart from fixed handle 22 and, correspondingly, second spaced-apart members 21a and 21b are in an initial non-rotated configuration for positioning tissue therebetween (FIG. 3A). Moveable handle 24 is depressible from this initial position to a depressed position corresponding to the second spaced-apart members 21a and 21b being in a rotated configuration (e.g., a "closed configuration") for compressing tissue (FIG. 3B) and/or electrosurgically treating tissue., e.g., sealing tissue.

Continuing with reference to FIG. 1A, outer shaft 12 is illustrated. Outer shaft 12 may be made from any suitable material. In particular, a suitable material provides an outer shaft 12 that is flexible enough to wind through a flexible endoscope but rigid enough to effectively transmit torsional forces from the movable handle 24 to inner shaft 20. This relatively flexible nature of the outer shaft 12 makes it suitable for use with "single incision laparoscopic surgery" (SILS) and "natural orifice translumenal endoscopic surgery" (NOTES) procedures. Suitable materials include but are not limited to metal, plastic, ceramic, etc. In the illustrated embodiment, outer shaft 12 is tubular and made from relatively pliable stainless steel. In some embodiments, however, the outer shaft 12 may be substantially rigid, i.e., outer shaft 12 is not able to move relative to the longitudinal axis "A-A".

Figure 1B:
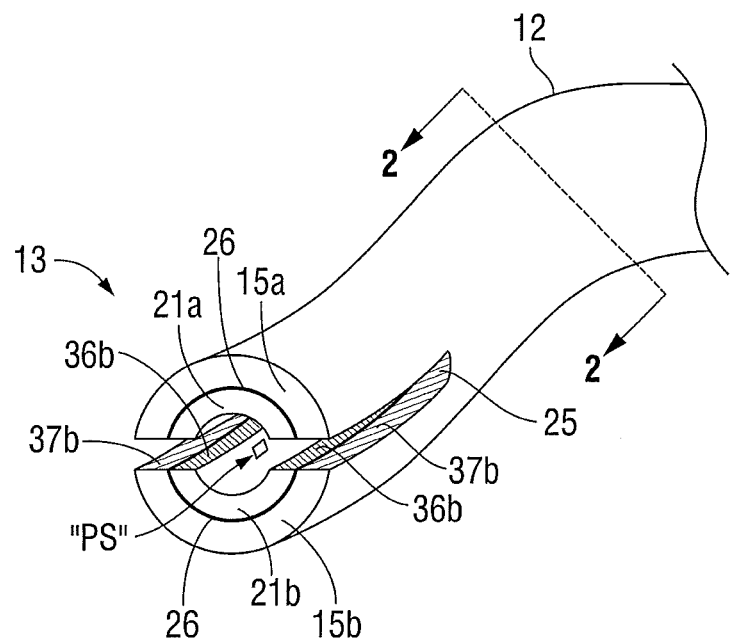
FIG. 1B is an enlarged area of detail depicted in FIG. 1A.
Figure 3B:
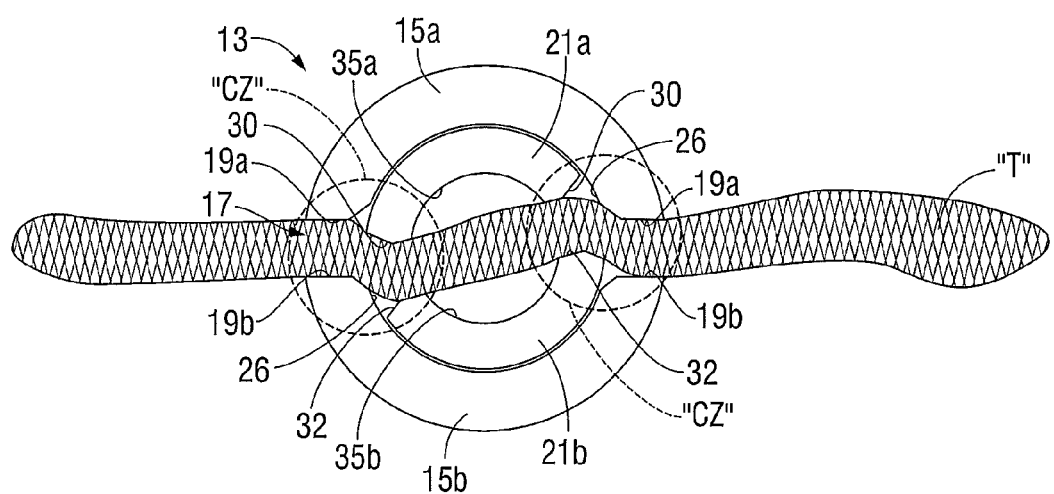

Outer shaft 12 extends from the housing 4 (FIG. 1A) and includes bifurcated distal end 13. Bifurcated distal end 13 includes a pair of first spaced-apart members 15a and 15b (FIGS. 1B and 3A-3B). In the illustrated embodiment, the first spaced-apart members 15a and 15b are formed on the outer shaft 12 during manufacturing thereof. In some embodiments, the first spaced-apart members 15a and 15b may be formed apart from the outer shaft 12 and, subsequently, coupled to the outer shaft 12 by one or more suitable coupling methods. In this instance, the first spaced-apart members 15a and 15b may be made from any suitable material including, but not limited to metal, plastic, ceramic, etc. First spaced-apart members 15a and 15b may include any suitable configuration to achieve the purposes described herein. For example, and in the illustrated embodiment, first spaced-apart members 15a and 15b are arcuate having a generally "C" configuration. This "C" configuration facilitates positioning tissue between the first spaced-apart members 15a and 15b.

An elongated slot 17 is defined through the first spaced-apart members 15a, 15b and is configured to receive tissue therethrough (FIGS. 3A-3B). The elongated slot 17 is defined by respective top and bottom walls 19a and 19b that meet at back walls 25 and 27 (see FIGS. 1B and 4, respectively). The height of the back walls 25, 27 is determined during the manufacturing process to accommodate various vessel sizes. As can be appreciated, back walls 25, 27 having relatively large heights are conducive in treating larger vessels, while back walls 25, 27 having relatively small heights are conducive in treating smaller vessels. In the illustrated embodiment, the back walls 25, 27 are configured to allow the first spaced-apart members 15a and 15b to flex thereabout, i.e., back walls 25, 27 function like a "living hinge;" which allows the surgeon to position tissue that is slightly larger than the opening of the elongated slot 17.

In the illustrated embodiment, the back walls 25, 27 may be made from non-conductive material to concentrate electrosurgical energy that is delivered to the electrodes 37a, 37b. Alternately, the back walls 25, 27 may be made from a conductive material and function to electrosurgically treat tissue.

Electrodes 37a, 37b are operably disposed on the respective top and bottom walls 19a, 19b and are in electrosurgical communication with the generator to provide electrosurgical current to electrosurgically treat tissue positioned between the first spaced-apart members 15a, 15b and second spaced-apart members 21a, 21b. In the illustrated embodiment, electrodes 37a, 37b extend longitudinally along a length of the top and bottom walls 19a, 19b. In certain instances, a plurality of intermittently-spaced electrodes 37a, 37b may be provided on each of the top and bottom walls 19a, 19b. The specific configuration of the electrodes 37a, 37b may depend on the contemplated uses of the instrument 2, a manufacturer's preference, type of tissue to be electrosurgically treated, etc. Moreover, these electrodes 37a, 37b may be independently related via a multiplexing circuit.

Figure 2:
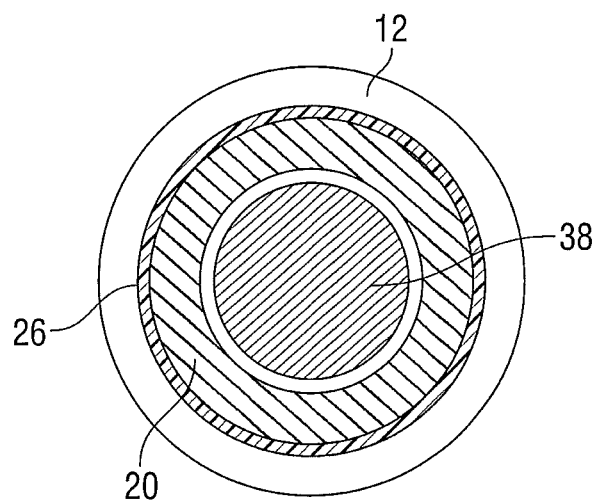
FIG. 2 is a cross-sectional view taken along line segment 2-2 in FIG. 1B.

With reference now to FIG. 2, in one embodiment, an insulative member 26, such as, for example, shrink wrap, is provided along an outer surface of the outer shaft 12 and is disposed between the inner and outer shafts 12, 20 and between first spaced-apart members 15a, 15b and second spaced-apart members 21a and 21b (FIG. 1B). For illustrative purposes, the insulative member 26 is not explicitly shown along the outer surface of the outer shaft 12. The insulative member 26 is configured to prevent short circuiting between the inner and outer shafts 12, 20 and between the first spaced-apart members 15a, 15b and second spaced-apart members 21a and 21b. To this end, the insulative member 26 may be made from any suitable material including, but not limited to, plastic, polymer, flouropolymer, ceramic and rubber. In the illustrated embodiment, the insulative member 26 is made from a relatively thin layer of thermoplastic or thermoset plastic.

Inner shaft 20 is shaped to complement the shape of the outer shaft 12 and is coaxially disposed therein (FIGS. 1A-3B). Inner shaft 20 may be made from the same material as outer shaft 12, such as in the illustrated embodiment. The inner shaft 20 is rotatable from an initial configuration (FIG. 3A) for positioning tissue between first spaced-apart members 15a, 15b and second spaced-apart members 21a and 21b, to a subsequent configuration for compressing the tissue therebetween at compression zone "CZ" to facilitate electrosurgically treating the tissue (FIG. 3B).

Figure 4:
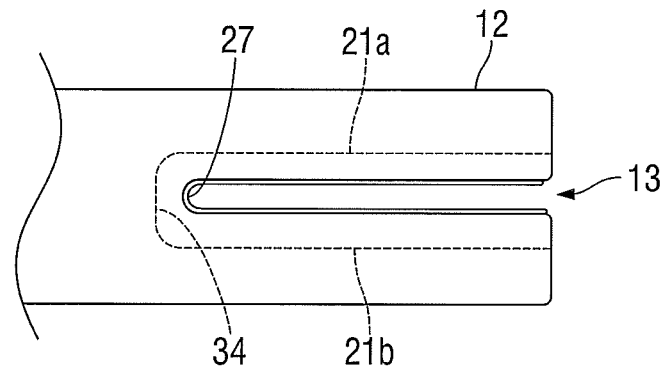
FIG. 4 is a right side view of the distal end of the shaft in an open configuration.

An elongated slot 28 is defined through the second spaced-apart members 21a, 21b and is configured to receive tissue "T" therethrough (FIG. 3A). Similar to that of elongated slot 17, the elongated slot 28 is defined by respective top and bottom walls 30 and 32 that meet at a back wall 34 (FIG. 4).

Similar to the first spaced-apart members 15a, 15b, the pair of second spaced-apart members 21a and 21b each includes a respective electrode 36a and 36b that is operably disposed thereon (FIG. 1B). The electrodes 36a and 36b are in electrosurgical communication with the generator (not shown) and are configured to provide electrosurgical current to electrosurgically treat tissue positioned between the first spaced-apart members 15a, 15b and second spaced-apart members 21a, 21b.

In the illustrated embodiment, the forceps 2 is configured to function in a bipolar mode of operation, e.g., electrosurgical energy is transmitted to both of the electrodes 36a, 36b and 37a, 37b. In other embodiments, however, forceps 2 may be configured to function in a monopolar mode of operation. In this instance, only one of the first spaced-apart members 15a, 15b or the second spaced-apart members 21a, 21b functions as an "active electrode" and separate return pad may be positioned on a patient and utilized as a "return electrode." In this instance, the "non-active" electrodes will be made from or coated with a non-conductive material.

In the bipolar mode of operation, electrosurgical energy may be delivered to the electrodes 36a, 36b and 37a, 37b via one or more suitable electrosurgical energy delivery protocols. For example, and in one particular embodiment, the forceps 2 may be configured such that electrosurgical energy is transferred from electrode 37a to corresponding electrode 36a and from electrode 37b to corresponding electrode 36b. Or, in another embodiment, the forceps 2 may be configured such that electrosurgical energy may be transferred from electrode 37a to electrode 36b and from electrode 37b to electrode 36a. Or, in yet another embodiment, the forceps 2 may be configured such that electrosurgical energy may be transferred from electrode 37a to electrode 37b and from electrode 36a to electrode 36b. Those skilled in the art will appreciate other delivery protocols that may be utilized with the forceps 2.

The wires of cable 18 couple, via one or more suitable coupling methods, to proximal ends of each of the outer and inner shafts 12 and 20 such that the outer and inner shafts 12 and 20 function as conduits to provide electrosurgical energy to the electrodes 36a, 36b and 37a, 37b. In this instance, the need to run wires through the relatively small area within the shaft 12 and/or shaft 20 is eliminated. As can be appreciated, this may reduce the overall manufacturing costs of the forceps 2.

Figure 5:
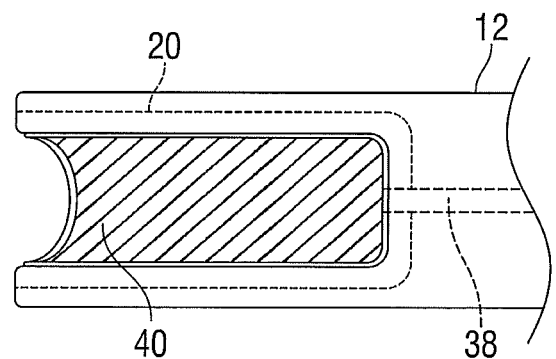
FIG. 5 is a left side view of the distal end of the shaft in an open configuration and with a cutting blade in a deployed configuration.

Each of the spaced-apart members 21a and 21b includes a longitudinal knife groove 35a and 35b that extends along a length thereof and is configured for reciprocation of a knife blade 40 therein (FIGS. 3A-3B and 5).

With reference to FIGS. 2 and 5, a cutting blade shaft 38 is operably coupled to the trigger assembly 10 and is translatable through the inner shaft 20 to move the knife blade 40 to sever tissue. Knife blade 40 is operably disposed at distal end of cutting blade shaft 38. The knife blade 40 is translatable from an initial configuration proximal the first spaced-apart members 15a and 15b and second spaced-apart members 21a and 21b (FIG. 1), to a subsequent configuration wherein the knife blade 40 is configured to sever tissue that has been electrosurgically treated, see FIG. 5, for example.

In operation of one embodiment, second spaced-apart members 21a and 21b are, initially, in a non-rotated configuration (FIGS. 1A-1B and 3A). Subsequently, tissue is positioned between the first spaced-apart members 15a and 15b and second spaced-apart members 21a and 21b. Thereafter, movable handle 24 is approximated toward fixed handle 22, which, in turn, rotates the inner shaft 20 within the outer shaft 12 (FIG. 3B). As inner shaft 20 rotates, second spaced-apart members 21a and 21b rotate and compress tissue positioned therebetween at compression zones "CZ." The edges of the first spaced-apart members 15a and 15b and second spaced-apart members 21a and 21b may be chamfered, beveled, or otherwise configured to facilitate compressing tissue, see FIGS. 3A and 3B for example.

Electrosurgical energy may then be transmitted to the electrodes 36a, 36b and 37a, 37b via one or more of the electrosurgical energy delivery protocols to electrosurgically treat the tissue.

In certain embodiments, such as, for example when tissue is to be sealed, one or more stop members (e.g., a "hard stop" not explicitly shown) or other suitable device, e.g., proximity sensors "PS" (FIG. 1B), accelerometers, etc., may be provided on the spaced-apart members 15a, 15b or 21a, 21b (or electrodes 36a, 36b and 37a, 37b) to provide a specific gap distance therebetween. In one embodiment, the proximity sensors "PS" may be configured to provide a gap distance that ranges from about 0.001 inches to about 0.006 inches between spaced-apart members 15a, 15b or 21a, 21b. In addition, the spaced-apart members 21a, 21b may be configured such that rotation thereof with respect the spaced-apart members 15a, 15b may provide a specific pressure on tissue when tissue is positioned between the spaced-apart members 15a, 15b and 21a, 21b. For example, a ratchet mechanism ("RM") or other suitable device may be provided on the forceps 2 to maintain a specific pressure on tissue (FIG. 1A). In one embodiment, the ratchet mechanism "RM" may be disposed within the housing 4 and operably coupled to the inner shaft 20 to incrementally lock the spaced-apart members 21a, 21b in one or more locked configurations. In embodiments, each of the locked configurations may correspond to a specific pressure that is to be applied on tissue when the tissue is positioned between the spaced-apart members 15a, 15b and 21a, 21b and the spaced-apart members 21a, 21b are rotated. The pressure applied to tissue may range from about 3 kg/cm$^3$ to about 16 kg/cm$^3$. Further, one or more controllers "C" (or control algorithms) may be operably coupled to the forceps 2 (or provided in the generator) to control the amount of electrosurgical energy that is provided to the electrodes 36a, 36b and 37a, 37b (FIG. 1A). In the illustrated embodiment, the controller(s) "C" (and operable components associated therewith) are disposed within the housing 4. All of these three factors may contribute in providing an effective, uniform and consistent tissue seal.

To sever the electrosurgically treated tissue (e.g., sealed tissue), movable handle 24 may be released, which, in turn, causes the inner shaft 20 to return to the non-rotated configuration and the trigger assembly 10 may be actuated to translate the cutting blade shaft 38 including the knife blade 40 distally (FIG. 5).

The unique configuration of the outer shaft 12 and inner shaft 20 including respective first spaced-apart members 15a and 15b and second spaced-apart members 21a and 21b provides an alternative method of electrosurgically treating tissue as compared to conventional forceps.

From the foregoing, and with reference to the various figure drawings, those skilled in the art will appreciate that certain modifications can also be made to the present disclosure without departing from the scope of the same. For example, in certain instances, one or more structures or devices (i.e., stop members) may be positioned between the inner and outer shafts 12 and 20 to limit movement of the inner shaft 20 with respect to the outer shaft 12.

In certain embodiments, it may prove advantageous to manufacture the inner and outer shafts 12 and 20 from a material other than metal, e.g., a non-conductive material, such as plastic. For example, and in one particular embodiment, the inner shaft 20 may be manufactured from a relatively pliable plastic and the outer shaft 12 may be manufactured from stainless steel. In this instance, the outer shaft 12 may be covered by the insulative material 26. Unlike the previously described embodiment, however, the insulative material 26 need not be positioned between the inner and outer shafts 12 and 20 as described above. That is, the plastic configuration of the inner shaft 20 provides an insulative barrier between the inner shaft 20 and outer shaft 12. Further, the electrodes 36a and 36b may be coupled to the second spaced-apart members 21a and 21b of the inner shaft 20 by one or more suitable coupling methods. In this embodiment, one or more of the wires of the cable 18 may be fed through the inner and/or outer shafts 20 and 12 and operably coupled to the electrodes 36a and 36b.

Moreover, and in some embodiments, the first spaced-apart members 15a and 15b and second spaced-apart members 21a and 21b may be configured to tension tissue in addition to (or instead of) compressing the tissue. In this particular instance, tissue may be tensioned as a result of the second spaced-apart members 21a and 21b being rotated with respect to the first spaced-apart members 15a and 15b, for example, tissue may be tensioned subsequent to treatment thereof to separate the treated tissue. This particular embodiment may have particular use when implementing a knife blade is not feasible, or impractical. In this instance, since a cutting blade shaft 38 including knife blade 40 is not utilized, a suction source may be provided and in operative communication with the forceps 2 to aspirate the severed tissue. This may prove useful in the instance when contact between the severed tissue and adjacent tissue is not desired, such as, for example, when the severed tissue is diseased (e.g., cancerous).

While the aforementioned configurations of the inner and outer shafts 12 and 20 have been described herein as being utilized with a forceps 2 that utilizes RF energy, it is within the purview of the present disclosure to utilize the inner and outer shafts 12 and 20 with devices other than the forceps 2. For example, and in some embodiments, the inner and outer shafts 12 and 20 may be utilized with ultrasonic devices that are configured to treat tissue, e.g., dissect, coagulate, seal, etc. In one particular embodiment, for example, the inner and outer shafts 12 and 20 may be utilized with a torsional ultrasonic device (not explicitly shown). In this instance, a transducer of the ultrasonic device may be operably coupled to the inner shaft 20 and configured to vibrate the inner shaft 20 as the inner shaft 20 is rotated to achieve one or more desired tissue effects.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for electrosurgically treating tissue, comprising:
   positioning tissue between pairs of first and second spaced-apart members of respective bifurcated distal ends of inner and outer shafts of an electrosurgical instrument, the pairs of first and second spaced-apart members each including at least one respective first and second electrode thereon, each of the at least one first and second electrodes adapted to connect to an electrosurgical energy source configured to supply electrosurgical energy thereto;
   rotating the inner shaft from an initial configuration to a subsequent configuration to compress the tissue between the pairs of first and second spaced-apart members;
   controlling a gap between the pairs of first and second spaced-apart members with a sensor when the inner shaft is in the subsequent configuration;
   regulating pressure applied to tissue positioned between the pairs of first and second spaced-apart members with a ratchet mechanism when the inner shaft is in the subsequent configuration;
   transmitting electrosurgical energy to the at least one first and second electrodes to seal tissue; and
   rotating the inner shaft to its initial configuration.

2. A method according to claim 1, wherein the gap between the pairs of first and second spaced-apart members when the inner shaft is in the subsequent position ranges from about 0.001 inches to about 0.006 inches and wherein the pressure applied to tissue when the inner shaft is in the subsequent position ranges from about 3 kg/cm$^3$ to about 16 kg/cm$^3$.

3. A method for electrosurgically treating tissue, comprising:
   positioning tissue between pairs of first and second spaced-apart members of respective bifurcated distal ends of inner and outer shafts of an electrosurgical instrument, the pairs of first and second spaced-apart members each including at least one respective first and second electrode thereon, each of the at least one first and second electrodes adapted to connect to an electrosurgical energy source configured to supply electrosurgical energy thereto;
   rotating the inner shaft from an initial configuration to a subsequent configuration to compress the tissue between the pairs of first and second spaced-apart members;
   transmitting electrosurgical energy to the at least one first and second electrodes to electrosurgically treat the tissue;
   translating a cutting blade shaft of the electrosurgical instrument within the inner shaft to sever the electrosurgically treated tissue; and
   rotating the inner shaft to its initial configuration.

4. A method according to claim 3, wherein electrosurgically treating tissue includes sealing tissue.

5. A method according to claim 4, further including the step of providing the electrosurgical instrument with a sensor configured to control a gap between the pairs of first and second spaced-apart members when the inner shaft is in the subsequent configuration.

6. A method according to claim 5, further including the step of providing the electrosurgical instrument with a ratchet mechanism configured to regulate pressure applied to tissue positioned between the pairs of first and second spaced-apart members when the inner shaft is in the subsequent configuration.

7. A method according to claim 6, wherein the gap between the pairs of first and second spaced-apart members when the inner shaft is in the subsequent position ranges from about 0.001 inches to about 0.006 inches and wherein the pressure applied to tissue when the inner shaft is in the subsequent position ranges from about 3 kg/cm$^3$ to about 16 kg/cm$^3$.

8. An electrosurgical instrument configured to treat tissue, comprising:
   a housing having a controller operably disposed therein, the controller configured to regulate electrosurgical energy transmitted via an electrosurgical energy source to the electrosurgical instrument;
   an outer shaft extending from the housing and defining a longitudinal axis therethrough, the outer shaft including a bifurcated distal end having a pair of first spaced-apart members with an elongated slot extending therebetween, the pair of first spaced-apart members configured to receive tissue therebetween, the pair of first spaced-apart members having at least one corresponding first electrode thereon adapted to connect to the electrosurgical energy source;
   an inner shaft disposed within the outer shaft, the inner shaft including a bifurcated distal end having a pair of second spaced-apart members with an elongated slot extending therebetween, the pair of second spaced-apart members configured to receive tissue therebetween, the pair of second spaced-apart members having at least one corresponding second electrode thereon adapted to connect to the electrosurgical energy source, wherein the inner shaft is rotatable from an initial configuration for positioning tissue between the pairs of first and second spaced-apart members to a subsequent configuration for compressing the tissue disposed between the pairs of first and second spaced-apart members to facilitate sealing the tissue upon activation of the at least one first and second electrodes;
   a ratchet mechanism operably disposed in the housing and configured to regulate pressure applied to tissue positioned between the pairs of first and second spaced-apart members when the inner shaft is in the subsequent configuration; and
   at least one sensor operably associated with at least one of the inner and outer shafts and configured to control a gap between the pairs of first and second spaced-apart members when the inner shaft is in the subsequent configuration.

9. An electrosurgical instrument according to claim 8, wherein the gap between the pairs of first and second spaced-apart members when the inner shaft is in the subsequent position ranges from about 0.001 inches to about 0.006 inches.

10. An electrosurgical instrument according to claim 9, wherein the pressure applied to tissue when the inner shaft is in the subsequent position ranges from about 3 kg/cm$^3$ to about 16 kg/cm$^3$.

11. An electrosurgical instrument according to claim 10, wherein a longitudinal groove extends along a length of each spaced-apart member of the pair of second spaced apart members and is configured for reciprocation of the knife blade therein.

12. An electrosurgical instrument according to claim 8, wherein the pressure applied to tissue when the inner shaft is in the subsequent position ranges from about 3 kg/cm$^3$ to about 16 kg/cm$^3$.

13. An electrosurgical instrument, comprising:
a housing;
an outer shaft extending from the housing and defining a longitudinal axis therethrough, the outer shaft including a bifurcated distal end having a pair of first spaced-apart members with an elongated slot extending therebetween, the pair of first spaced-apart members configured to receive tissue therebetween, the pair of first spaced-apart members having at least one corresponding first electrode thereon adapted to connect to an electrosurgical energy source;
an inner shaft disposed within the outer shaft, the inner shaft including a bifurcated distal end having a pair of second spaced-apart members with an elongated slot extending therebetween, the pair of second spaced-apart members configured to receive tissue therebetween, the pair of second spaced-apart members having at least one corresponding second electrode thereon adapted to connect to the electrosurgical energy source; and
a cutting blade shaft that is translatable through the inner shaft, wherein the inner shaft is rotatable from an initial configuration for positioning tissue between the pairs of first and second spaced-apart members to a subsequent configuration for compressing the tissue disposed between the pairs of first and second spaced-apart members to facilitate electrosurgically treating the tissue upon activation of the at least one first and second electrodes.

14. An electrosurgical instrument according to claim 13, wherein the cutting blade shaft includes a knife blade at distal end thereof, the knife blade translatable with the cutting blade shaft from an initial position proximal the pair of second spaced-apart members to a subsequent position therebetween for severing tissue.

15. An electrosurgical instrument according to claim 14, wherein a longitudinal groove extends along a length of each spaced-apart member of the pair of second spaced apart members and is configured for reciprocation of the knife blade therein.

16. An electrosurgical instrument according to claim 13, wherein an insulative member is operably disposed between the pairs of first and second spaced-apart members.

17. An electrosurgical instrument according to claim 16, wherein the insulative member is selected from the group consisting of plastic, rubber and ceramic.

18. An electrosurgical instrument according to claim 13, wherein the outer shaft is flexible.

19. An electrosurgical instrument according to claim 13, wherein each of the first and second electrodes is further defined by a plurality of intermittently-spaced electrodes.

20. An electrosurgical instrument according to claim 13, wherein the electrosurgical instrument includes a movable handle that is configured to rotate the inner shaft within the outer shaft to effect movement of the pair of second spaced-apart members with respect to the pair of first spaced apart members.

* * * * *